US006911153B2

(12) United States Patent
Minter

(10) Patent No.: US 6,911,153 B2
(45) Date of Patent: Jun. 28, 2005

(54) METHOD AND APPARATUS FOR TREATING FLUID MIXTURES WITH ULTRASONIC ENERGY

(75) Inventor: Bruce E. Minter, Eagle, ID (US)

(73) Assignee: The Halliday Foundation, Inc., Boise, ID (US)

( * ) Notice: Subject to any disclaimer, the term of this patent is extended or adjusted under 35 U.S.C. 154(b) by 116 days.

(21) Appl. No.: 10/176,334

(22) Filed: Jun. 19, 2002

(65) Prior Publication Data

US 2002/0195402 A1 Dec. 26, 2002

Related U.S. Application Data

(60) Provisional application No. 60/300,580, filed on Jun. 22, 2001.

(51) Int. Cl.[7] .............................. C02F 1/36; C02F 1/78; B01J 19/10
(52) U.S. Cl. ...................... 210/748; 210/750; 210/760
(58) Field of Search ................................ 210/748, 750, 210/758, 760, 764

(56) References Cited

U.S. PATENT DOCUMENTS

| 2,363,247 | A | * | 11/1944 | Holder ........................ 203/39 |
| 2,417,722 | A | * | 3/1947 | Wolff ........................ 210/748 |
| 2,717,768 | A | | 9/1955 | Carpentier .................. 366/114 |
| 2,896,922 | A | | 7/1959 | Pohlman ..................... 366/109 |
| 3,686,115 | A | * | 8/1972 | Farman et al. .............. 210/748 |
| 4,003,832 | A | * | 1/1977 | Henderson et al. ......... 210/728 |
| 4,071,225 | A | | 1/1978 | Holl ............................ 366/114 |
| 4,076,617 | A | | 2/1978 | Bybel et al. .................. 210/19 |
| 4,428,757 | A | | 1/1984 | Hall ............................. 96/175 |
| 4,556,467 | A | | 12/1985 | Kuhn et al. ................. 204/193 |
| 4,597,876 | A | * | 7/1986 | Hall ........................... 210/748 |
| 4,747,920 | A | * | 5/1988 | Muralidhara et al. ....... 204/542 |
| 4,944,886 | A | * | 7/1990 | Masri ......................... 210/748 |
| 5,164,094 | A | * | 11/1992 | Stuckart ..................... 210/708 |
| 5,192,450 | A | * | 3/1993 | Heyman ..................... 210/748 |
| 5,370,740 | A | * | 12/1994 | Chao et al. ................... 134/1 |
| 5,372,634 | A | * | 12/1994 | Monahan ..................... 96/175 |
| 5,466,367 | A | | 11/1995 | Coate et al. ................ 210/252 |
| 5,508,975 | A | * | 4/1996 | Walter .......................... 95/30 |
| 5,679,257 | A | | 10/1997 | Coate et al. ................ 210/695 |
| 5,728,305 | A | | 3/1998 | Hawkinson ................. 210/760 |
| 5,902,489 | A | * | 5/1999 | Yasuda et al. .............. 210/748 |
| 6,299,761 | B1 | | 10/2001 | Wang .......................... 210/87 |
| 6,361,698 | B1 | | 3/2002 | Tai ............................. 210/760 |

OTHER PUBLICATIONS

The Chemistry of Ultrasound by Kenneth S. Suslitk, from Yearbook of Science & the Future 1994; Encyclopaedia Britannica: Chicago. 1994, pp 138–155.

(Continued)

*Primary Examiner*—Fred G. Prince
(74) *Attorney, Agent, or Firm*—Joseph W. Holland

(57) ABSTRACT

A method and apparatus for treating mixtures with ultrasonic energy. In one embodiment, the mixture can include a selected constituent and the method can include directing a continuous flow of the mixture into a treatment apparatus and altering a phase and/or a chemical composition of the selected constituent by exposing the mixture to ultrasonic energy while the mixture flows through the apparatus. The mixture can then be removed from the apparatus. In one aspect of this embodiment, the mixture can be under pressure while being exposed to the ultrasonic energy and the mixture can subsequently be exposed to a vacuum source to remove gas from the mixture. In another aspect of the invention, the ultrasonic energy can have a first frequency and the mixture can be exposed to ultrasonic energy of a second frequency different than the first frequency while in the apparatus. The ultrasonic energy can cavitate a liquid portion of the mixture to generate heat that can kill pathogens in the mixture (when the selected constituent includes pathogens) and/or oxidize the selected constituent to produce an ash and a gas.

10 Claims, 3 Drawing Sheets

OTHER PUBLICATIONS

Nitric Oxide Formation by Ultrasound in Aqueous Solutions by Vladimir Misik & Peter Riesz: Published by the American Chemical Society. 1996, J. Phys. Chem 100. pp. 17986–17994.

The Removal of Bacterial Biofilm from Water–Filled Tubes Using Axially Propagated Ultrasound by Mott, Stickley Coakley and Bott: Journal of Applied Microbiology 1998, B4, pp 509–514.

* cited by examiner

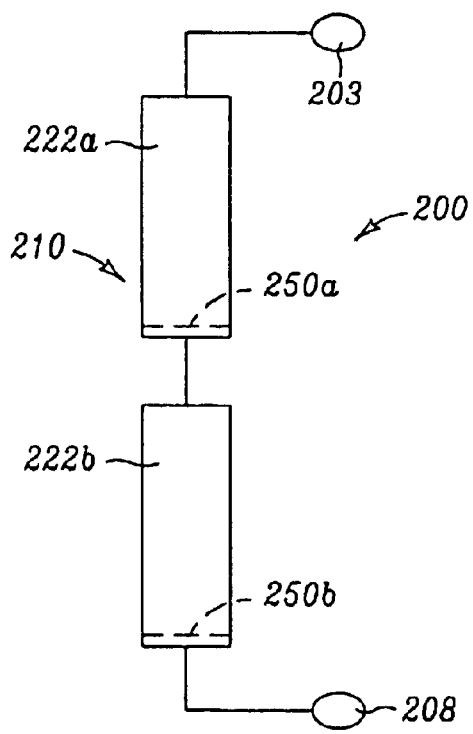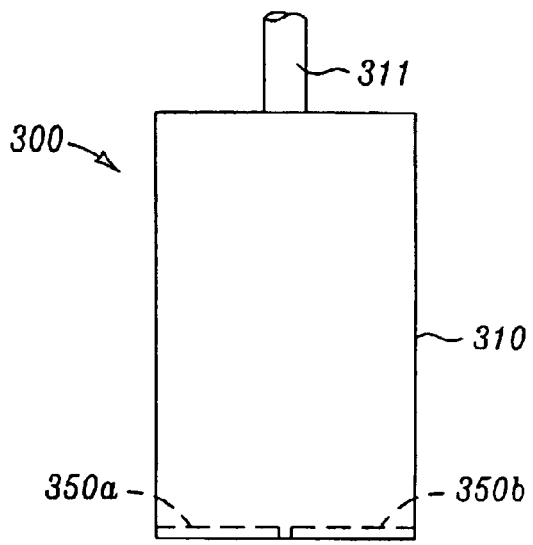
Fig. 3A              Fig. 3B
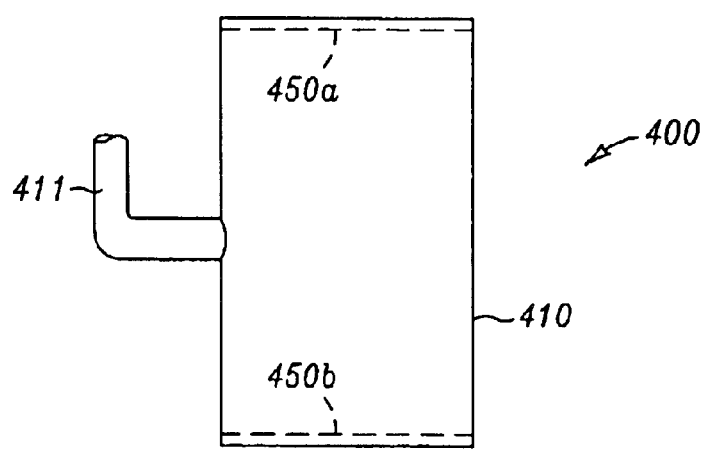
Fig. 3C

METHOD AND APPARATUS FOR TREATING FLUID MIXTURES WITH ULTRASONIC ENERGY

RELATED APPLICATIONS

This application claims the benefit of U.S. Provisional Application No. 60/300,580 filed Jun. 22, 2001. This application is also related to the following application assigned to a common assignee (a) "Ozone Generator", application Ser. No. 10/123,759 filed Apr. 15, 2002; and the following applications filed concurrently herewith (b) Method and Apparatus for Treating Fluid Mixtures with Ultrasonic Energy, filed Jun. 20, 2002, Ser. No. 10/176,728; (c) Method and Apparatus for Directing Ultrasonic Energy, filed Jun. 20, 2002, Ser. No. 10/177,578; (d) and Method and Apparatus for Directing Ultrasonic Energy, filed Jun. 19, 2002, Ser. No. 10/176,333, which are all herein incorporated by reference.

BACKGROUND

1. Technical Field

The present invention relates to methods and apparatuses for treating mixtures, such as agricultural or industrial waste streams, with ultrasonic energy to clean or otherwise alter the waste streams.

2. Background

Many industrial, municipal and agricultural processes generate waste matter that is potentially harmful to the environment. Accordingly, a variety of processes have been developed to remove harmful elements from the waste matter before returning the water to lakes, streams and oceans. Many conventional processes include filters, such as reverse osmosis filters that remove solid contaminants from the waste matter. However, because of environmental concerns, it may be difficult to dispose of the solid contaminants removed by the filters. Furthermore, the filters themselves must be periodically back-flushed, which can be a time consuming process. Accordingly, in one alternative process, microorganisms are disposed in the waste matter to consume or alter harmful elements in the waste matter. However, such systems generally process the waste matter in a batch mode and accordingly may be slow and labor intensive to operate. Another conventional approach is to sterilize waste matter streams with ultraviolet light. One problem with this approach is that the waste matter must be positioned very close to the light source, which can make ultraviolet systems slow, expensive and inefficient. Still another method includes exposing the waste matter stream to ozone, which can alter harmful elements in the waste matter stream. One problem with this approach is that the cost of generating effective quantities of ozone is generally so high that the process may not be economically feasible.

Yet another conventional approach is to expose the waste matter stream to ultrasonic energy. For example, one conventional method includes disposing the waste matter in a vessel and applying ultrasonic energy to the waste matter in a batch process. This conventional approach suffers from several drawbacks. For example, the batch process can be relatively slow. Furthermore, the efficiency with which ultrasonic energy is transmitted to the waste matter may be so low as to leave an unacceptable level of contaminants in the waste matter stream.

SUMMARY

The present invention is directed toward methods and apparatuses for treating mixtures with ultrasonic energy. A method in accordance with one aspect of the invention includes introducing into a treatment apparatus a continuous flow of a mixture (such as an aqueous mixture) that includes a selected constituent (such as a contaminant). A phase and/or a chemical composition of the selected constituent is altered by exposing the mixture to ultrasonic energy while the mixture flows through the apparatus. The mixture is then removed from the apparatus.

In a further aspect of the invention, exposing the mixture to ultrasonic energy can including cavitating a liquid portion of the mixture to generate heat. Altering a chemical composition of the selected constituent can include oxidizing the selected constituent to produce an ash and a gas. The mixture can be under pressure while it is exposed to ultrasonic energy and can be coupled to a vacuum source after being exposed to the ultrasonic energy to remove gas from the mixture. In still a further aspect of the invention, the ultrasonic energy can include a first ultrasonic energy having a first frequency and the mixture can be exposed to a second ultrasonic energy having a second frequency different than the first frequency.

The invention is also directed toward an apparatus for treating a selected constituent in a mixture that includes the selected constituent. In one aspect of the invention, the apparatus can include a vessel having an entrance port and an exit port, with the entrance port being configured to receive a first continuous flow of the mixture during operation and the exit port being configured to simultaneously expel a second continuous flow of the mixture. The apparatus can further include a source of ultrasonic energy operatively coupled to the vessel to continuously transmit ultrasonic energy to the mixture at an energy level and frequency sufficient to gasify and/or alter a chemical composition of the selected constituent as the mixture moves through the vessel from the entrance port to the exit port during operation. The ultrasonic energy source can one of two ultrasonic energy sources, and the vessel can include first and second channels coupled to each other, with one of the two ultrasonic energy sources positioned to direct first ultrasonic energy into the first channel and the other ultrasonic energy source positioned to direct second ultrasonic energy into the second channel as the mixture passes through the first and second channels.

BRIEF DESCRIPTION OF THE DRAWINGS

FIGS. 3A–3C are schematic illustrations of treatment apparatuses in accordance with further embodiments of the invention.

DETAILED DESCRIPTION

The present disclosure describes apparatuses and methods for treating waste matter, such as aqueous waste streams. Many specific details of certain embodiments of the invention are set forth in the following description and in FIGS. 1–3C to provide a thorough understanding of these embodiments. One skilled in the art, however, will understand that the present invention may have several additional embodiments, or that the invention may be practiced without several of the details described below.

Overall System

Figure 1:
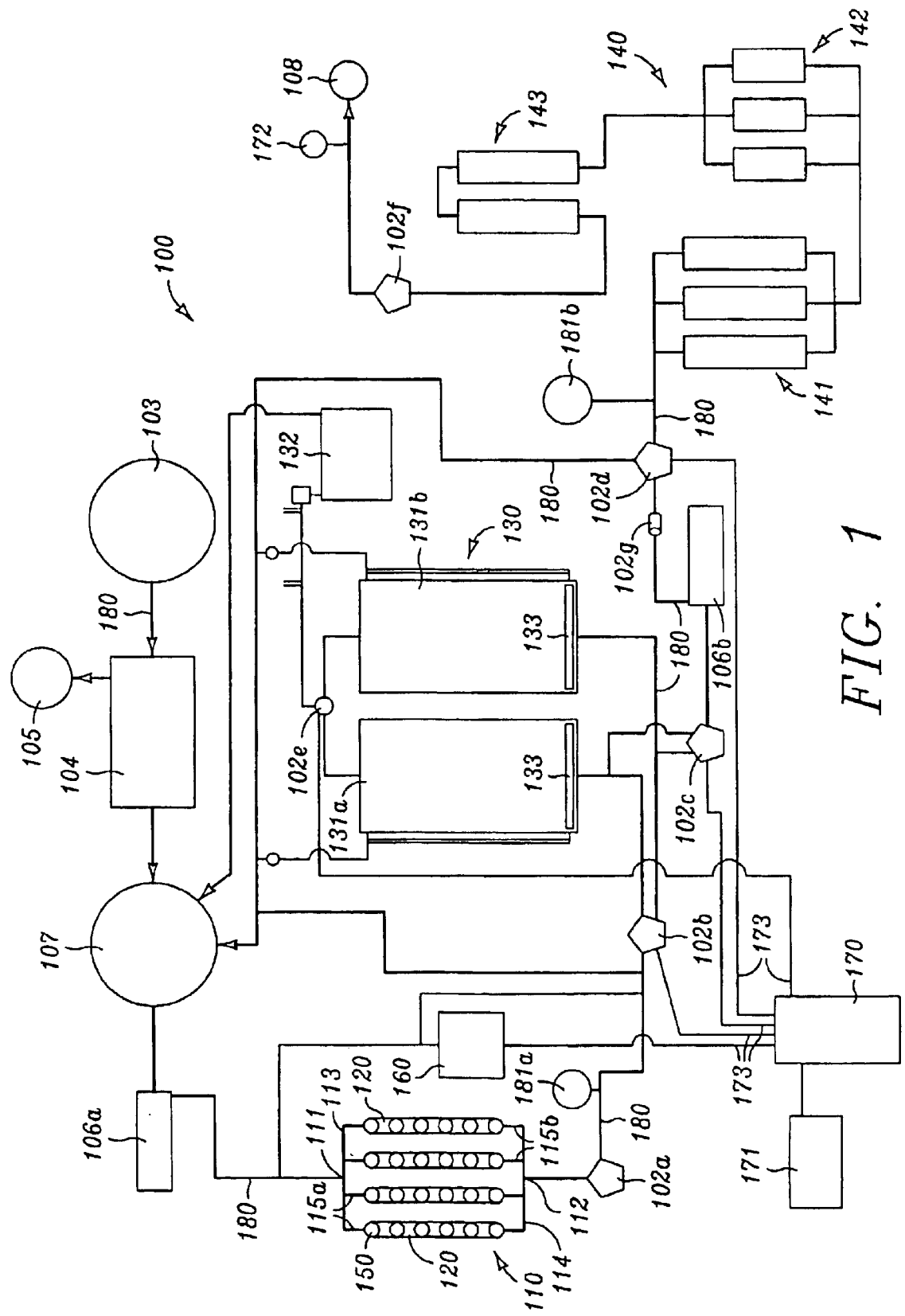
FIG. 1 is a schematic diagram of an apparatus in accordance with an embodiment of the invention.

FIG. 1 is a block diagram schematically illustrating components of an apparatus 100 in accordance with an embodiment of the invention. In one aspect of this embodiment, the apparatus 100 can include a source 103 of waste matter coupled with connecting conduits 180 to a vessel 110. The vessel 110 can include one or more channel assemblies 120 having ultrasonic energy sources 150 that direct ultrasonic energy into the waste matter flow to gasify and/or alter a chemical structure of constituents in the waste matter flow. The flow can proceed via additional connecting conduits 180 to a degassing assembly 130 where gaseous components are removed from the flow. The degassed stream can then proceed to a separation assembly 140 where solid components which may have been generated in the vessel 110 are removed from the flow. The flow exits the apparatus 100 through an outflow port 108 and can then be re-used or returned to the environment. In one aspect of this embodiment, the waste matter stream can proceed in a continuous manner from the source 103 to the outflow port 108. Alternatively, the apparatus 100 can operate in a batch mode, as will be described in greater detail below with reference to FIGS. 3B–3C.

In one embodiment, the apparatus 100 can further include a solids separator 104 between the source 103 and the vessel 110. The solid separator 104 can remove a selected quantity of solids suspended in the waste matter and direct the removed solids to a solids dump 105. Removing at least a portion of the solids from the waste matter stream upstream of the vessel 110 can improve the efficiency with which the apparatus 100 operates, as will be described in greater detail below. The waste matter flow can proceed from the solids separator 104 to a holding chamber 107. A pump 106a can withdraw the waste matter from the chamber 107, pressurize the waste matter, and direct the waste matter to the vessel 110 via the connecting conduits 180. In one embodiment, the pressure of the waste matter entering the vessel 110 can be from about 5 psi to about 40 psi, but in other embodiments the pressure of the waste matter entering the vessel 110 can be outside of this range.

In one embodiment, the vessel 110 can include an entrance port 111 that receives a continuous flow of the waste matter, and an exit port 112 through which the partially treated waste matter exits the vessel 110. In one aspect of this embodiment, the vessel 110 can be configured to divide the waste matter stream into several components that are processed in parallel in the channel assemblies 120 and recombined before exiting the vessel 110 through the exit port 112. Accordingly, the vessel 110 can include an intake manifold 113 for dividing the incoming flow upstream of the channel assemblies 120 and an output manifold 114 for collecting the flow downstream of the channel assemblies 120. The intake manifold 113 can further include a plurality of intake manifold conduits 115a, each of which directs a portion of the incoming waste matter into one of the channel assemblies 120. The output manifold conduits 115b collect the flows from the channel assemblies 120 upstream of the exit port 112.

Channel Assembly

Figure 2:
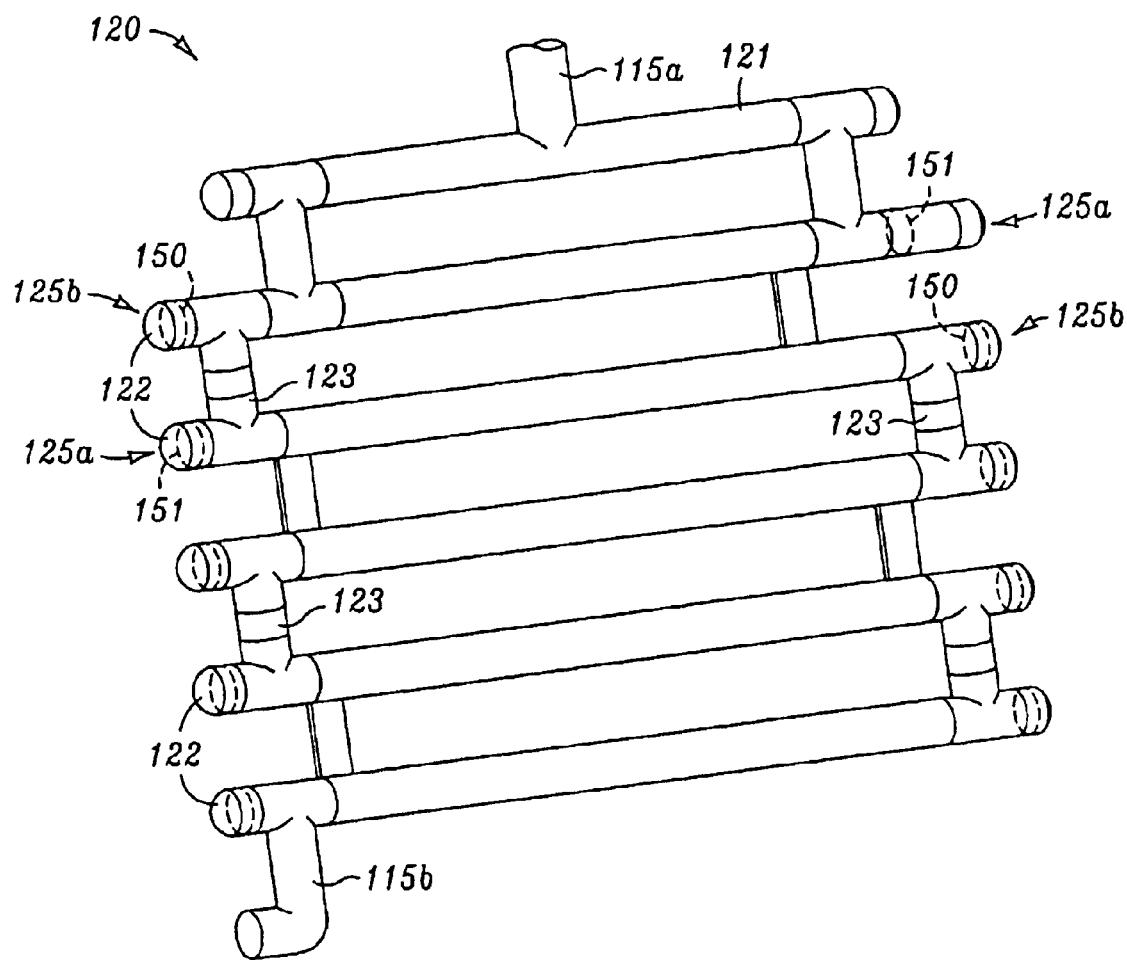
FIG. 2 is a partially schematic, isometric view of a channel assembly that forms a portion of the apparatus shown in FIG. 1 in accordance with an embodiment of the invention.

FIG. 2 is an isometric view of one of the channel assemblies 120 shown in FIG. 1. In one embodiment, the channel assembly 120 can include an assembly manifold 121 that directs the waste matter flow from the intake manifold conduit 115a into a plurality of serially arranged channels 122 connected with connecting conduits 123. Each channel 122 can be an elongated tube having a first end 125a and a second end 125b, and can be supported relative to adjacent channels with struts 124. The waste matter stream proceeds generally from the first end 125a of each channel 122 to the second end 125b, then through the connecting conduit 123 to the first end 125a of the next channel 122. The waste matter stream passes from the last channel 122 into the output manifold conduit 115b, and then to the vessel exit port 112 (FIG. 1).

In one embodiment, an ultrasonic energy source 150 (such as a piezo-electric source or another ultrasonic energy emitter or generator) is positioned toward the second end 125b of each channel 122. Accordingly, the waste matter can travel toward the ultrasonic energy source 150 as it moves through the channel 122. Alternatively, the ultrasonic energy source 150 can be positioned toward the first end 125a of each channel 122 with the waste matter traveling away from the ultrasonic energy source 150. In either embodiment, the end of the channel 122 opposite the ultrasonic energy source 150 can include a reflector 151 positioned to reflect (a) at least a portion of the ultrasonic energy generated by the ultrasonic energy source 150, and/or (b) products produced by the ultrasonic energy, such as cavitation bubbles. Accordingly, the reflector 151 can direct the ultrasonic energy and/or the products produced by the ultrasonic energy back toward the ultrasonic energy source 150. Additional details of devices that focus and reflect ultrasonic energy and/or resulting products are provided in a copending patent application assigned to the assignee of the present application and titled "Method and Apparatus for Directing Ultrasonic Energy" Ser. No. 60/300,355. Whether or not the channel assembly 120 includes reflectors 151, the sources 150 can be selected to emit ultrasonic energy at a power and frequency that cause an aqueous (or other liquid) portion of the waste matter stream to cavitate. Accordingly, cavitation bubbles formed in the waste matter stream can grow in a cyclic fashion and ultimately collapse. This process creates very high temperatures, pressures, and thermal cycling rates. For example, it is estimated that this process can develop temperatures in the waste matter stream of up to 5,000 degrees Celsius, pressures of up to 1,000 atmospheres, and heating and cooling rates above 10 billion degrees Celsius per second for durations of less than 1 microsecond (see, for example, Suslick, "The Chemistry of Ultrasound," in The Yearbook of Science and the Future, Encyclopedia Britannica, 138–145 (1994), incorporated herein in its entirety by reference).

The temperatures and pressures developed by the collapsing cavitation bubbles can have several advantageous effects on the constituents of the waste matter stream. For example, the collapsing bubbles can form radicals, such as OH radicals which are unstable and can chemically interact with adjacent constituents in the waste matter stream to change the chemical composition of the adjacent constituents. In one such process, the OH radical can interact with nitrates in the waste matter stream to produce gases such as nitrogen dioxide. The following are sample steps in such a reaction:

1) $NO_3^- + \cdot OH \rightarrow \cdot NO_3 + OH^-$
2) $\cdot NO_3^- + \cdot OH \rightarrow HO_2 \cdot + \cdot NO_2$
3) $\cdot NO_2 + \cdot NO_2 \rightarrow \cdot NO + \cdot NO_3$
4) $\cdot NO_2 + \cdot NO_2 \rightarrow \cdot NO + \cdot NO + O_2$
5) $\cdot NO_2 + \cdot H \rightarrow \cdot NO + \cdot OH$
6) $\cdot NO_2 + \cdot OH \rightarrow \cdot NO + HO_2 \cdot$
7) $\cdot NO_2 + \cdot O \cdot \rightarrow \cdot NO_2 + O_2$ In another embodiment, the reaction can continue (for example, in the presence of additional constituents) to produce nitrites. In yet another embodiment, the cavitating bubble can alter trichloroethylene, for example, in accordance with the following simplified reaction:

$$(Cl)_2C=CHCl+2H_2O \rightarrow \ldots \rightarrow Cl_2+HCl+2H_2+2CO \qquad (1)$$

In other embodiments, the collapsing cavitation bubbles can have effects on other molecules that change a chemical composition of the molecules and/or change a phase of the molecules from a liquid or solid phase to a gaseous phase. In still further embodiments, the collapsing cavitation bubbles can have other effects on other constituents of the waste matter stream. For example, the high pressures and temperatures generated by the collapsing cavitation bubbles can disrupt the molecular structure of the walls of living cells and can accordingly kill and break up pathogenic organisms, such as bacteria. Another effect of the collapsing cavitation bubbles can be to combust or oxidize constituents of the waste matter stream. For example, the high temperature produced by the collapsing cavitation bubble can oxidize constituents of the waste matter stream, producing by-products such as carbon dioxide and ash. The carbon dioxide can evolve from the waste matter stream and the ash can be filtered from the waste matter stream, as will be described in greater detail below.

In still another embodiment, the collapsing cavitation bubbles can also separate constituents of the waste matter stream. For example, when the waste matter stream includes a mixture of oil, water, and an emulsifier, the collapsing cavitation bubbles can alter the molecular characteristics of the emulsifier and cause the emulsifier to loose its effectiveness. Accordingly, the oil and water can separate from each other and one or the other can be removed from the stream. The collapsing cavitation bubbles can have other effects on the waste matter stream that alter the characteristics of the constituents of the stream in a manner that makes the constituents more benign and/or allows the constituents to be more easily removed from the waste matter stream. In any of these embodiments, several characteristics of the channel assembly 120 can be selected to have desired effects on the waste matter stream. In any of these embodiments, several characteristics of the channel is assembly 120 can be selected to have desired effects on the waste matter stream. For example, the frequency of the ultrasonic energy transmitted by the sources 150 into the waste matter stream can be selected based on the resonant frequencies of constituents in the waste matter stream. In one particular embodiment, the frequency of the ultrasonic energy source 150 can be selected to be at or above a natural resonant frequency of molecules of constituents in the stream. In one further specific example, when the flow includes farm animal fecal waste in an aqueous solution, along with pathogens such as *E. coli*, the ultrasonic energy sources 150 can be selected to produce a distribution of ultrasonic waves having an energy peak at approximately 980 kilohertz. In other embodiments, the peak energy of the ultrasonic energy sources 150 can be selected to occur at other frequencies, depending for example on the types, relative quantities, and/or relative potential harmful effects of constituents in the stream. Accordingly, individual ultrasonic energy sources 150 can be selected to have a particular, and potentially unique, effect on selected constituents of the waste matter stream.

In another embodiment, adjacent ultrasonic energy sources within one or more of the channel assemblies 120 can produce different frequencies. For example, the ultrasonic energy source 150 in the uppermost channel 122 of FIG. 2 can emit energy at a higher frequency than that emitted by the energy source 150 in the next downstream channel 122. An advantage of this arrangement for waste matter streams having multiple constituents (each of which is best affected by ultrasonic energy at a different frequency) is that the waste matter streams can be subjected to a plurality of frequencies, with each frequency tailored to affect a particular constituent of the waste matter stream. Such an arrangement can be more effective than some conventional arrangements for removing constituents from the waste matter stream in a single apparatus.

The geometry of the channel assembly 120 can be selected to define the time during which any given constituent of the waste matter stream is subjected to the energy emitted by the ultrasonic energy sources 150. For example, the overall length of the flow path through each channel assembly 120 and the rate at which the waste matter stream passes through the channel assembly 120 can be selected according to the amount of suspended solids in the waste matter stream, with the overall residence time within the channel assembly 120 being lower for waste matter streams having relatively few suspended solids and higher for waste matter streams having more suspended solids. Accordingly, each channel assembly 120 can be made smaller (by reducing the number of channels 122 in each assembly 120) and/or faster (by increasing the flow rate of the waste matter through the channel assembly) when the solids separator 104 (FIG. 1) filters out a greater fraction of the suspended solids.

Returning now to FIG. 1, the apparatus 100 can include features that increase the number of radicals and/or other chemically reactive constituents in the waste matter stream. For example, the apparatus can include an ozone generator 160 coupled to the vessel 110 to introduce ozone into the waste matter stream while the ultrasonic energy sources 150 are activated. In other embodiments, the ozone generator 160 can be replaced with, or supplemented by, sources of other chemically reactive species. In any of these embodiments, gas generated by the chemical reactions in the vessel 110 can be removed from the waste matter stream, as will be described in greater detail below. The non-gas molecules remaining in the waste matter stream after the gas is formed can either be removed from the waste matter stream or can remain in the waste matter stream depending, for example, on the potential hazard to the quality of the waste matter presented by the remaining molecules.

In one embodiment, the waste matter stream can proceed from the vessel 110 toward the degassing assembly 130 via the connecting conduits 180. In one aspect of this embodiment, the apparatus 100 can include a valve 102a, such as a throttling valve, that allows the portion of the waste matter stream upstream of the valve 102a to have a pressure greater than atmospheric pressure, while the portion of the waste matter stream downstream of the valve 102a can be subjected to a pressure less than atmospheric pressure. Accordingly, the pressure within the degassing assembly 130 can be reduced to increase the rate at which gas evolves from the mixture, without reducing the pressure of the mixture within the vessel 110.

The degassing assembly 130 can include two gas release chambers 131 (shown as a first chamber 131a and a second chamber 131b) coupled to the connecting conduits 180 with a selector valve 102b. The selector valve 102b can be configured to alternate between a first setting with the waste matter stream directed into the first gas release chamber 131a and a second setting with the waste matter stream directed into the second gas release chamber 131b. The waste matter stream exiting the vessel 110 can accordingly be directed into the first gas release chamber 131a until the first chamber 131a is filled to a desired level, and then directed in the second gas release chamber 131b.

While the second gas release chamber 131b is filling, the filled first gas release chamber 113a can be subjected to a vacuum pressure generated by a vacuum source 132 coupled to the gas release chambers 131 with a valve 102e. After the waste matter has resided in the first gas release chamber 131 a under vacuum for a time sufficient to remove a selected amount of gas from the waste matter stream, the stream exits the first chamber 131a and the first chamber 131a is re-filled while a vacuum is applied to the waste matter in the second chamber 131b. Accordingly, the continuous flow of waste matter from the vessel 110 can be sequentially directed into either the first or second gas release chamber 131a, 131b without interrupting the flow. In one embodiment, the vacuum source 132 can remain in fluid communication with both chambers 131 during both the transient "fill" and the steady state "filled" portions of the cycle for each chamber. Alternatively, the vacuum source 132 can be coupled to each chamber 131 only after that chamber has been filled. In either embodiment, the vacuum source 132 can increase the speed with which gas in the waste matter is removed.

In an alternate embodiment, the gas release chambers 131 can be open to the atmosphere to release gas from the waste matter stream under atmospheric pressure. Whether the waste matter is subject to atmospheric pressure or less than atmospheric pressure, the fluid within the chambers 131 can be agitated, for example, with an agitation device 133. In one aspect of this embodiment, the agitation device 133 can include a piezo-electric energy source that generates ultrasonic energy in the gas release chambers 131. Alternatively, the agitation device 133 can generate pressure waves at other frequencies. In still further embodiments, the agitation device 133 can include other devices, such as stirrers or other mechanical implements.

After exiting the degassing assembly 130, the waste matter stream proceeds to the separation assembly 140 via a connecting conduit 180. A valve 102c can be selectively adjusted to drain flow from whichever gas release chamber 131 has completed its cycle. A boost pump 106b can pressurize the waste matter stream to direct the stream through a check valve 102g and into first, second and third filter stages 141, 142 and 143 in the separation assembly 140. In one embodiment, the first filter stage 141 can include multi-media 15 micron filter elements, the second filter stage 142 can include 2 micron filter elements and the third filter stage 143 can include activated charcoal. In another embodiment, the separation assembly 140 can include other separation arrangements. For example, when the apparatus 110 operates to deactivate an emulsifier in an oil/water mixture, the separation assembly 140 can be configured to separate one or more of the oil, the water, and the emulsifier from the remaining constituents. In any of these embodiments, a back pressure valve 102f can control the back pressure through the separation assembly 140, and a flow meter 172 can monitor the rate of flow through the apparatus 100. When the flow meter 172 is positioned adjacent to the outflow port 108 (as shown in FIG. 1), the flow rate determined by the flow meter 172 may be less than a flow rate measured at the source 103 because gas may be removed from the flow at the degassing assembly 130 and solids may be removed from the flow in the separation assembly 140.

In one embodiment, the operations of the apparatus 100 can be automatically controlled with a controller 170. In one aspect of this embodiment, the controller 170 is operatively coupled to a pneumatic source 171 to direct and regulate flows of pressurized air to the controlled elements via pneumatic lines 173. The apparatus 100 can include other automatic control features, such as fail-safe devices in valves 102b and 102d that close these valves automatically in the event of a power failure to direct the waste matter stream back to the waste matter holding chamber 107. Surge suppression tanks 181a and 181b can be positioned along the flow path between the source 103 and the outflow port 108 to absorb fluctuations in the flow volume and pressure throughout the apparatus 100.

One feature of an embodiment of the apparatus 100 described above with reference to FIGS. 1 and 2 is that the waste matter stream flows in a continuous fashion from the source 103 to the outflow port 108. An advantage of this feature is that the treatment of the waste matter throughout the apparatus 100 can be more consistent and faster than for conventional batch systems. Another feature of an embodiment of the apparatus 100 is that the channel assemblies 120 can have a modular construction. Accordingly, the channel assemblies 120 can be easily formed to have as long or as short a flow path as is appropriate for the type of flow directed into the assemblies.

Still a further advantage is that the vessel 110 can include channel assemblies 120 having different flow path lengths. For example, each of the channel assemblies 120 shown in FIG. 1 can have a different flow path length, and instead of directing equal portions of the waste matter stream through each channel assembly 120, the entire waste matter stream can be directed through the channel assembly 120 having the length corresponding to the desired residence time appropriate for the amount of solids suspended in that waste matter stream. Accordingly, an embodiment of the apparatus 100 can be suitable for treating a variety of different waste matter streams.

Still another feature of an embodiment of the apparatus 100 described above with reference to FIGS. 1 and 2 is that the vessel 110 can include a plurality of ultrasonic energy sources 150, each emitting ultrasonic energy at a different frequency. Accordingly, each ultrasonic energy source 150 can be selected to have a desired effect on a particular constituent of the waste matter stream. In one aspect of this embodiment, a plurality of ultrasonic energy sources 150 having different frequencies can be disposed in each channel assembly 120. Alternatively, all the ultrasonic energy sources 150 in a particular channel assembly 120 can emit ultrasonic energy at the same frequency, but the frequency selected for each channel assembly 120 can be different. Accordingly, the apparatus 100 can be compatible with a variety of different waste matter streams by directing a selected waste matter stream through the channel assembly 120 having ultrasonic energy sources 150 that emit energy at the frequency most appropriate for the constituents in that waste matter stream.

Further Systems

FIGS. 3A–3C are schematic illustrations of portions of treatment apparatuses in accordance with other embodiments of the invention. For purposes of illustration, only portions of the apparatuses are shown in FIGS. 3A–3C, and it will be understood that the apparatuses can include additional elements that are generally similar to those described above with reference to FIGS. 1 and 2.

FIG. 3A illustrates a portion of an apparatus 200 that includes a waste matter source 203, an outflow port 208 and a vessel 210 between the source 203 and the outflow port 208. In one aspect of this embodiment, the vessel 210 can include two channels 222 (shown as a first channel 222a and a second channel 222b) coupled together in a series arrangement. The first channel 222a can include a first ultrasonic energy source 250a that emits ultrasonic energy at a first frequency, and the second channel 222b can include a second ultrasonic energy source 250b that emits ultrasonic energy at a second frequency different than the first frequency. Accordingly, the apparatus 200 can direct ultrasonic energy at different frequencies into the same waste matter stream to selectively affect different constituents within the waste matter stream, as described above with reference to FIGS. 1–2. Alternatively, the first and second energy sources 250a and 250b can emit ultrasonic energy at the same frequency. In either embodiment, each channel 222 can include a single length of a tube, a series of channel segments that double back on each other (similar to those shown in FIG. 2), a non-tubular chamber, or any liquid-tight container.

FIG. 3B illustrates an apparatus 300 that operates in a batch mode and includes a vessel 310 having an entrance/exit port 311 and first and second ultrasonic energy sources 350a and 350b. As was generally described above with reference to FIGS. 1–3A, the first ultrasonic energy source 350a can emit ultrasonic energy at a first frequency, and the second ultrasonic energy source 350b can emit ultrasonic energy at a second frequency different than the first frequency. The ultrasonic energy sources 350a, 350b can be placed at any position within the vessel 310 for which the ultrasonic energy can be efficiently transmitted to the waste matter stream. For example, both ultrasonic energy sources 350a, 350b can be positioned at one end of the vessel 310 and, in one embodiment, an ultrasonic reflector (not shown) can be positioned at the opposite end. In any of the embodiments described above with reference to FIG. 3B, one feature of the apparatus 300 is that it can be used in situations where a batch operation is preferred to a continuous flow operation.

FIG. 3C illustrates an apparatus 400 having a vessel 410 with an entrance/exit port 411 and two ultrasonic energy sources 450 (shown as a first source 450a and second source 450b) at opposite ends of the vessel 410. Accordingly, the energy sources 450 can be operated either simultaneously or sequentially to create cavitation bubbles in a volume of waste matter within the vessel 410. In one aspect of this embodiment, each of the energy sources 450 can be configured and positioned to reduce potential wear caused by energy emitted by the other energy source 450.

From the foregoing it will be appreciated that specific embodiments of the invention have been described herein for purposes of illustration, but that various modifications may be made without deviating from the spirit and scope of the invention. For example, several embodiments of the invention have been described in the context of an aqueous mixture or waste matter stream, and in other embodiments, the mixture may not include water. In still another embodiment, the apparatus can include first and second vessels and can receive a continuous flow of waste matter that is alternately directed into each vessel. The first vessel can be filled first, after which the continuous flow is directed into the second vessel. While the second vessel is filling, ultrasonic energy can be directed into the mixture in the first vessel, and while the first vessel is filling, ultrasonic energy can be directed into the mixture in the second vessel. Accordingly, the apparatus can take in a continuous flow of waste matter that is divided and exposed to ultrasonic energy in separate batch processes. Accordingly, the invention is not limited except as by the appended claims.

I claim:

1. A method for removing contaminants from water, comprising:

introducing a continuous flow of a mixture of the water and the contaminants into a treatment apparatus;

introducing ultrasonic energy into the mixture as the mixture flows continuously through the treatment apparatus to alter a molecular composition of at least one of the contaminants and generate a gas;

applying a vacuum to the mixture to remove at least some of the gas from the mixture as the mixture flows through the treatment apparatus;

directing the mixture into a first channel;

transmitting ultrasonic energy to the mixture from a first ultrasonic energy generator while the mixture flows through the first channel;

directing the mixture into a second channel; and transmitting ultrasonic energy to the mixture from a second ultrasonic energy generator while the mixture flows through the second channel.

2. The method of claim 1 wherein the ultrasonic energy is a first ultrasonic energy and wherein the method further comprises introducing a second ultrasonic energy to the mixture.

3. The method of claim 1, further comprising filtering solid materials from the mixture after applying a vacuum to the mixture.

4. The method of claim 1, further comprising pressurizing the mixture and introducing ultrasonic energy into the mixture while the mixture flows under pressure.

5. The method of claim 1, further comprising directing the mixture into a channel having a length corresponding to a level of suspended solids in the mixture.

6. The method of claim 1, further comprising removing at least a portion of the contaminants from the mixture after exposing the contaminants to the ultrasonic energy and while the mixture flows continuously through the apparatus.

7. The method of claim 1 wherein the ultrasonic energy includes a first ultrasonic energy having a first frequency, and wherein the method further comprises exposing the contaminants to a second ultrasonic energy having a second frequency different than the first frequency.

8. The method of claim 1 wherein the ultrasonic energy includes a first ultrasonic energy having a first frequency, and wherein the method further comprises exposing the contaminants to a second ultrasonic energy having a second frequency different than the first frequency after exposing the contaminants to the first frequency.

9. The method of claim 1 wherein a molecular structure of a component of the mixture has a resonant frequency, and wherein the method further comprises selecting a frequency of the ultrasonic energy to be at or above the resonant frequency of the component of the mixture.

10. The method of claim 1, further comprising introducing ozone into the mixture before exposing the contaminants to ultrasonic energy.

* * * * *